United States Patent [19]

Homma et al.

[11] 4,160,023

[45] Jul. 3, 1979

[54] **TOXOIDS DERIVED FROM PROTEASE AND ELASTASE OF *PSEUDOMONAS AERUGINOSA* AND PRODUCTION THEREOF**

[75] Inventors: Yuzuru Homma, Tokyo; Kazuyuki Morihara, Osaka, both of Japan

[73] Assignee: Shionogi & Co., Ltd., Japan

[21] Appl. No.: 764,454

[22] Filed: Jan. 31, 1977

[30] Foreign Application Priority Data

Feb. 5, 1976 [JP] Japan .................................. 51-10836
Feb. 5, 1976 [JP] Japan .................................. 51-10837

[51] Int. Cl.$^2$ ...................... A61K 39/40; A61K 39/02
[52] U.S. Cl. ........................................ 424/87; 424/92; 424/94
[58] Field of Search .................. 424/85, 87, 88, 92, 424/94

[56] References Cited

U.S. PATENT DOCUMENTS

| | | | |
|---|---|---|---|
| 2,528,972 | 11/1950 | Pillemer | 424/92 |
| 3,135,662 | 6/1964 | Pope et al. | 424/92 |
| 3,658,986 | 4/1972 | Tompkins et al. | 424/88 |
| 3,674,863 | 7/1972 | Fisher et al. | 424/92 |
| 3,928,565 | 12/1975 | Homma et al. | 424/92 |
| 3,968,202 | 7/1976 | Stein | 424/92 |
| 3,983,229 | 9/1976 | Relyveld | 424/92 |
| 3,987,164 | 10/1976 | Homma et al. | 424/92 |
| 4,079,126 | 3/1978 | Homma et al. | 424/92 |

OTHER PUBLICATIONS

Jones, Journal of Hygiene (Cambridge) 67:241-247 (1969) "Detoxification of an Immunogenic Fraction from a Culture Filtrate of *Pseudomonas aeruginosa*".

Liu et al., J. Inf. Dis. 128(4):520-526, Oct. 1973, "Exotoxins of *Pseudomonas aeruginosa* III, Characteristics of Antitoxin A".

Pavlovskis et al., Microbiology, pp. 252-256 (1975) "*Pseudomonas aeruginosa* Exotoxin".

Callahan, Infection and Immunity 14(1):55-56 (Jul. 1976), *Pseudomonas aeruginosa* Exotoxin: purification by Preparative Polyacrylamide Gel Electrophorosis and the Development of a Highly Specific Antitoxin Serum.

Markley and Smallman, J. Bact. 96(4):867-874, Oct. 1968, "Protection by Vaccination Against Pseudomonas Infection after Thermal Injury".

Lusis et al., Vet. Bull., 41(3):169-177, Mar. 1971, "*Pseudomonas aeruginosa*".

*Primary Examiner*—Shep K. Rose
*Attorney, Agent, or Firm*—Wenderoth, Lind & Ponack

[57] ABSTRACT

Toxoids derived from protease and elastase of *Pseudomonas aeruginosa* which are effective to prevent infections caused by *Pseudomonas aeruginosa* and production thereof.

22 Claims, No Drawings

TOXOIDS DERIVED FROM PROTEASE AND ELASTASE OF *PSEUDOMONAS AERUGINOSA* AND PRODUCTION THEREOF

This invention relates to toxoids derived from protease and elastase of *Pseudomonas aeruginosa* and production thereof. Furthermore, it relates to prevention and treatment of infections caused by *P. aeruginosa* by inoculating the toxoids.

Infections by *P. aeruginosa* have been a serious problem in the medical field. The infectious diseases are observed in immature infants, newborn infants or leukemia and cancer patients at the terminal stage. Such diseases cause infections and weakened defense mechanisms. In the field of veterinary medicine, hemorrhagic pneumonia in minks caused by *P. aeruginosa* and mammitis in bovines caused by *P. aeruginosa* create a serious economic problem in the livestock industry.

Only a few antibiotics against *P. aeruginosa* have been developed recently, but they are insufficiently effective. Meanwhile, protease and elastase produced from some species of *P. aeruginosa* have been found to be one of the pathogens of the infections caused by *P. aeruginosa* exemplified above (K. Kawaharajo et al., Japan J. Exp. Med., 45, 79–88 (1975); Japan. J. Exp. Med., 45, 515 (1975); Japan. J. Exp. Med., 44, 435–442 (1974); J. Y. Homma et al., Japan J. Exp. Med., 45, 89–100(1975)).

Attempts have been made to prepare toxoids derived from protease and elastase of *P. aeruginosa* to suppress the infections caused by *P. aeruginosa*. The toxoids provided by the present invention are effective to suppress the infections caused by *P. aeruginosa* singly or in combination. The efficacy is remarkable, particularly when they are combined with the original endotoxin protein (OEP) isolated by one of the inventors of the present invention (J. Y. Homma et al., Japan. J. Exp. Med., 45, 355–360 (1975); J. Y. Homma et al., Japan. J. Exp. Med., 42, 23–34 (1972); J. Y. Homma, Microbial Drug Resistance, Tokyo University Press, Tokyo 267–279 (1975); J. Y. Homma, The Fourth International Congress of Animal, Plant and Microbial Toxins, Plenum Publisher, London (1975)). The toxoids are also available to prepare anti-serum and antibody which are used in vaccination and medical treatment.

The physicochemical properties of the toxoids are as follows:

Toxoid of protease from *P. aeruginosa*

(1) Molecular weight: 63000(gel filtration)
(2) Ultraviolet absorption spectrum: maximum 280 mµ ($E_{1\%}^{280}$ 9.27, 0.1 M KCl), minimum 250 mµ
(3) Isoelectric point: pH 5.2 (forcal electrophoresis)
(4) Constituent amino acids: (amino acid (g)/100 g of protein) aspartic acid (15.6), glutamic acid (9.5), leucine (8.7), alanine (8.5), glycine (7.7), serine (7.6), tyrosine (6.9), phenylalanine (5.9), threonine (5.0), valine (5.0), lysine (4.1), isoleucine (3.9), arginine (2.3), tryptophan (2.3), proline (2.1), histidine (1.9), ammonia (1.4), (total 98.5 g)
(5) Appearance: colorless powder
(6) Antigen activity: positive
(7) Protease activity: negative

Toxoid of elastase from *P. aeruginosa*

(1) Molecular weight: 47000(gel filtration)
(2) Ultraviolet absorption spectrum: maximum 278 mµ ($E_{1\%}^{278}$ 21.2, 0.1 M KCl), minimum 252 mµ
(3) Isoelectric point: pH 6.5 (electrophoresis with cellulose acetate membrane)
(4) Constituent amino acids: (amino acid (g)/100 g of protein) aspartic acid (14.2), tyrosine (9.9), phenylalanine (7.0), glutamic acid (6.5), arginine (6.5), alanine (5.8), glycine (5.6), serine (5.6), threonine (5.0), valine (4.9), leucine (4.3), lysine (3.9), methionine (2.9), proline (2.9), isoleucine (2.7), histidine (2.6), tryptophan (2.3), cystine/2 (1.2), ammonia (0.9), (total 94.7 g)
(5) Appearance: colorless powder
(6) Antigen activity: positive
(7) Elastase activity: negative The toxoids with the above properties are novel and useful in medical and veterinary medical fields.

The toxoids are manufactured in a usual manner. Protease or elastase from *P. aeruginosa* is dissolved in a suitable buffer with pH 6 to 10, e.g. borate buffer, acetate buffer, phosphate buffer, glycine buffer, or tris buffer. A buffer having pH 9 is preferred. To the enzyme solution in a buffer is added formalin or oxymethanesulfinic acid until the enzyme is inactivated. In the case of protease, formalin is advantageously used in a concentration of 4 to 10% (v/v) and oxymethanesulfinic acid being 0.4 to 3 M in the presence of lysine. Arginine, leucine, tyrosine, glutamic acid, and the like can be used instead of lysine, but lysine is most preferred. In the case of elastase, formalin is used in a concentration of 1 to 6% (v/v) and oxymethanesulfinic acid is 0.25 to 5 M. The preparation is effected at 10° to 40° C., preferably at room temperature. The reaction period almost depends on other reaction condition, while it is 1 to 7 days under the favorable condition, preferably 3 days or more for inactivating the enzyme.

The production and properties of the protease are described in Japanese Patent Publication No. 27315/1965; K. Morihara et al., Biochem. Biophys. Acta., 73, 113, 125 (1963); Biochem. Biophys. Acta., 92, 351, 361 (1964); Arch. Biochem. Biophys., 114, 158 (1966); Biochem. Biophys. Acta., 309, 414 (1973); Agr. Biol. Chem., 38 (3), 621 (1974). Those of the elastase are described in the above patent publication; K. Morihara et al., J. Biol. Chem., 240, 3295 (1965); J. Bacteriol., 88, 745 (1964); Arch. Biochem. Biophys., 123, 572 (1968); Agr. Biol. Chem., 39, 1123 (1975).

The efficacy of the thus-obtained toxoids (abbreviated as protease toxoid and elastase toxoid) is demonstrated by immune tests on rabbits, mice and minks.

Experiment 1    Antigenicity Test on Rabbits (1) Methods:
(a) Protease Toxoid: Protease toxoid (1 mg) is subcutaneously inoculated to three New Zealand white rabbits with Freund's incomplete adjuvant. After 1 week, protease toxoid (1 mg) is again subcutaneously injected followed by intramuscular inoculateions of protease toxoid (1 mg) at intervals of two weeks, two weeks, three weeks and one week successively. Blood is collected from ear vein at a certain time intervals. A blood serum is separated and heated at 56° C. to measure passive hemagglutinative (PHA) titer by the method described in Japan. J. Exp. Med. Vol. 45, No. 5, 361 (1975), i.e. passive hemagglutination reaction using protease as antigen. (b) Elastase Toxoid: Elastase toxoid is inoculated to New Zealand white rabbits in the same manner as described in (a), but inoculation is performed 4 times at intervals of 2 weeks. The passive hemogglutinative (PHA) titer is measured by passive hemagglutination reaction using elastase as antigen.

(2) Results:

(a) Protease Toxoid (FIG. 1)

| Inoculation No. | 1st | 2nd | 3rd | 4th | 5th |
|---|---|---|---|---|---|
| Protease Toxoid | 1 mg* | 1 mg* | 1 mg | 1 mg | 1 mg |
| Administration Route** | s.c. | s.c. | i.m. | i.m. | i.m. |
| (Interval) | ↓ (2 weeks) | ↓ (2 weeks) | ↓ (2 weeks) | ↓ (3 weeks) | ↓ (1 week) |
| PHA Titer | ↑ | ↑ | ↑ | ↑ | ↑ | ↑ |
| Rabbit No. 1 | 0 | 512 | 1024 | 1024 | 1024 | 1024 |
| No. 2 | 0 | 128 | 256 | 256 | 256 | 256 |
| No. 3 | 0 | 128 | 512 | 512 | 512 | 4096 |

(b) Elastase Toxoid (FIG. 2)

| Inoculation No. | 1st | 2nd | 3rd | 4th |
|---|---|---|---|---|
| Elastase Toxoid | 1 mg* | 1 mg* | 1 mg | 1 mg |
| Administration Route** | s.c. | s.c. | i.m. | i.m. |
| (Interval) | ↓ (2 weeks) | ↓ (2 weeks) | ↓ (2 weeks) | ↓ (2 weeks) |
| PHA Titer | ↑ | ↑ | ↑ | ↑ | ↑ |
| Rabbit No. 1 | 0 | 64 | 512 | 512 | 4096 |
| No. 2 | 0 | 0 | 0 | 64 | 2048 |
| No. 3 | 0 | 8 | 123 | 128 | 512 |

Note:
*Inoculation with Freund's incomplete adjuvant
**s.c. = subcutaneous injection i.m. = intramuscular injection

Experiment 2   Antigenicity Test on Minks (a) Protease Toxoid: Thirteen Sapphire minks are intramuscularly inoculated protease toxoid (1000 γ) with adjuvant (potassium alum). The second vaccination is performed with the toxoid (500 γ) about 2 weeks later. The PHA titer against protease increased 64 to 512 (resiprocal serum of dilution) although the PHA titer is not observed before the vaccination.

(b) Elastase Toxoid: Twenty Sapphire minks are intramuscularly inoculated with elastase toxoid (500 γ) with adjuvant (potassium alum). The second vaccination of the toxoid (500 γ) is performed with adjuvant about two weeks later. After three weeks, the minks are inoculated the toxoid (1000 γ) with adjuvant. Blood is collected from the minks 18 days after the last inoculation. The PHA titer against elastase increases 16 to 60 (reciprocal serum of dilution), although the PHA titer is not observed before the inoculation.

Experiment 3

Enzyme Neutralizing Activity of Rabbit Serum Vaccinated with Toxoids (1) Methods:

(a) Protease-neutralizing activity is examined by measuring protease activity. A rabbit serum vaccinated with protease toxoid and a normal rabbit serum are tested. The PHA titer of the vaccinated serum is 7860. The PHA titer of the normal serum is negative against protease, elastase and OEP. The sera are heated at 56° C. for 30 minutes. A certain desired amount of protease is dissolved in 1/15 M phosphate buffer (pH 7.4). To the protease solution (0.2 ml) is added the serum to test (0.2 ml) and then physiological saline to make the whole volumn to 3.0 ml. The mixture is kept at 37° C. for 60 minutes. The remaining protease activity is measured by the method described below.

To the solution obtained above in a desired concentration is added a 2% (v/v) casein solution (1 ml, .pH 7.4). The mixture is incubated at 40° C. for 10 minutes followed by addition of a solution (2 ml) containing 0.1 M trichloroacetic acid, 0.2 M acetic acid and 0.2 M sodium acetate to stop enzyme activity. The mixture is kept at the same temperature for 20 minutes to precipitate unreacted casein completely and then is filtered. A quantity of tyrosine is measured with the filtrate by the Foline method. Namely, to the filtrate (1 ml) is added 0.4 M solution (5 ml) of sodium carbonate and a 20% (v/v) solution of Phenol Reagent Solution (produced by Nakai Chemical Co., Kyoto, the acid concentration 1.8 N). After 15 to 20 minutes, the absorbance of the mixture is measured at 670 mμ. The quantity of free tyrosine is calculated by comparing with the value obtained from the toxoid-casein mixture not incubated. (b) Elastase-neutralizing activity is tested by measuring elastase activity. Two rabbit sera immunized with elastase toxoid and normal rabbit serum are tested. The PHA titers of the vaccinated sera are 2048 and 256, respectively. The PHA titer of the normal serum is negative against protease, elastase and OEP. The sera to test are heated at 56° C. for 30 minutes. To the serum (0.2 ml) is added an elastase solution (0.2 ml) and then physiological saline to make the whole volumn to 2 ml. The solution is allowed to stand at 37° C. for 60 minutes.

The remaining elastase activity is measured by the method described in (a).

(2) Results:

(a) Protease Neutralizing Activity of Rabbit Serum Vaccinated with Protease Toxoid (Table 1)

| Protease γ/0.2 ml | Remaining Protease Activity (Neutralizing Activity) (OD 670 mμ) | | |
|---|---|---|---|
| | Vaccinated Serum* | Normal Serum | Without Serum |
| 0 | 0.058 (7860) | 0.07 | 0.045 |
| 10 | 0.062 (1920) | 0.15 | 0.105 |
| 20 | 0.060 (240) | 0.21 | 0.17 |
| 40 | 0.25 (<120) | 0.38 | 0.30 |
| 80 | 0.46 (<120) | 0.55 | 0.46 |
| 160 | 0.75 (<120) | 0.70 | 0.76 |

(b) Elastase Neutralizing Activity of Rabbit Serum Vaccinated with Elastase Toxoid (Table 2)

| Elastase γ/0.2 ml | Remaining Elastase Activity (Neutralizing Activity) (OD 670 mμ) | | | |
|---|---|---|---|---|
| | Vaccinated Serum* | | Normal Serum | Without Serum |
| | lot. 1 | lot. 2 | | |
| 0 | 0.05 (1920) | 0.06 (240) | 0.10 | 0.04 |
| 4.6 | 0.05 (960) | 0.06 (<120) | 0.26 | 0.16 |
| 9.2 | 0.06 (480) | 0.08 | 0.39 | 0.32 |
| 18.4 | 0.06 (120) | 0.34 | 0.62 | 0.50 |
| 36.8 | 0.21 (<120) | 0.80 | 1.04 | 0.87 |
| 73.6 | 0.94 (<120) | 1.16 | 1.33 | 1.24 |
| 147.2 | 1.52 (<120) | 1.42 | 1.48 | 1.45 |

Note:
*Figures in the parenthesis indicate PHA titer.

Experiment 4

Protective Effect against Infection of a Three-component Mixed Vaccine Containing OEP, Protease Toxoid and Elastase Toxoid (1) Method: Effect for protection against infection is tested on minks immunized by simple vaccine containing OEP alone or a three-component mixed vaccine containing OEP, protease toxoid and elastase toxoid.

Animals: 5 to 6 month-old female minks (Sapphire).

Application of vaccine: Subcutaneous or intramuscular injection.

Challenge test: The strain No. 5 of *P. aeruginosa* is used. Infection by live bacteria is effected by pouring the bacterial solution (0.5 ml) into the nasal cavity through a vinyl tube under etheral anesthesia.

Preparation of vaccines: (i) Protease toxoid-potassium alum solution: Protease toxoid (100 mg) is dissolved in a phosphate-buffered aqueous sodium chloride solution (M/15, pH 7.4) (PBS) (24.8 ml), and 10% potassium alum solution (2.5 ml) is added thereto. To the resultant solution, 20% $Na_2HPO_4 \cdot 12H_2O$ solution (2.5 ml) is further added, and the pH is adjusted to 6.5 to cause complete precipitation. Finally, a 1% themerosal solution (0.3 ml) as the antiseptic is added thereto (1 mg protease toxoid/0.3 ml). (ii) Elastase toxoid-potassium alum solution: The preparation is carried out in the same manner as mentioned above but using elastase toxoid in place of protease toxoid. (iii) OEP-potassium alum solution: OEP (100 mg) is dissolved in 0.01 N NaOH solution (5 ml), and PBS (28 ml) is added thereto. To the resultant solution, a 10% potassium alum solution (3.3 ml) and a 20% $Na_2HPO_4$ solution (3.3 ml) are added in order, and finally 1% thimerosal solution (0.4 ml) is added (1 mg OEP/0.4 ml). (iv) Three component mixed vaccine: Immediately before the use, the above prepared protease toxoid-potassium alum solution, elastase toxoid-potassium alum solution and OEP-potassium alum solution are mixed together. In 0.5 ml of this mixed solution, 500 γ of protease toxoid, 500 γ of elastase toxoid and 500 γ of OEP are contained.

Infection and immunization: Date of immunization, dosage, date of infection and date of autopsy are shown in Table 3.

Table 3

| Animal | Antigen* | Date of Immunization | | | Date of Challenge | Date of Autopsy |
|---|---|---|---|---|---|---|
| | | 8/18 | 8/30 | 9/18 | 10/7 | 10/20 |
| Group A | OEP | 500 γ | 500 γ | 1000 γ | 19th day after final injection for immunization | 13th day after challenge |
| Group B | OEP + Protease toxoid + Elastase toxoid | 500 γ  1000 γ  1000 γ | 500 γ  500 γ  500 γ | 1000 γ  1000 γ  1000 γ | 19th day after final injection for immunization | 13th day after challenge |

Note:
*Group A and Group B contain 1% potassium alum as adjuvant.

(2) Results:

Table 4.

| Number of Bacteria for Infection | Number of Minks | | | | | | | | | | |
|---|---|---|---|---|---|---|---|---|---|---|---|
| | Untreated | | | | Group A | | | | Group B | | |
| | The Day of Death After the Challenge | | | | | | | | | | |
| | 1 | 2 | 4 | 7 | 1 | 2 | 3 | Survival | 1 | 2 | 3 | Survival |
| $2 \times 10^5$ | 1 | | 1 | | | | | | | | | |
| $6 \times 10^5$ | | | | | | 2 | | 3 | | | | 2 |
| $2 \times 10^6$ | 1 | 1 | | | | | | | | | | |
| $6 \times 10^6$ | | | | | | 2 | | 3 | | | | 5 |
| $2 \times 10^7$ | 1 | | 1 | | | | | | | | | |
| $6 \times 10^7$ | | | | | | 4 | 1 | | | | | 5 |
| $2 \times 10^8$ | 1 | 1 | | | | | | | | | | |
| $6 \times 10^8$ | | | | | | 3 | 1 | 1 | 2 | | 1 | 2 |
| $2 \times 10^9$ | 2 | | | | | | | | | | | |
| $6 \times 10^9$ | 3 | 2 | | | | | | | 2 | | | 4 |
| $LD_{50}$ | $3.4 \times 10^{3*}$ | | | | $\leq 3.6 \times 10^{6**}$ | | | | $> 1.9 \times 10^9$ | | | |

Note:
*The number is obtained by the past experiments not a result of this experiment.
**A-B $P<0.01$ As shown in the above experiments, inoculation of toxoids of the present invention results in production of PHA titer and neutralizing antibody. They are effective against infections by *P. aeruginosa*, especially when combined with OEP.

Toxocity of toxoids derived from protease and elastase is very weak. Intraperitoneal administration (i.p.) to mice with a dose of 1 mg/mouse does not show any acute toxicity, the minimum lethal dose of protease being 0.2 mg/mouse (i.p.) and that of elastase 0.125 mg/mouse (i.p.).

The toxoids of this invention can be applied to human beings and animals to prevent infections by *P. aeruginosa*.

The application of the toxoids can be effected singly or in combination. Furthermore, they may be used with OEP. The inoculation may be practised subcutaneously, intramuscularly, or intracutaneously, if desired, with adjuvant. The toxoids may also be used to produce anti-serum against protease or elastase of P. aeruginosa. Antibody is collected from the anti-serum. The thus obtained anti-serum and antibody can be used to prevent infections caused by *P. aeruginosa*.

The vaccine of the toxoids can be manufactured in the usual method for preparing vaccines for human beings and animals. Namely, the toxoids are dissolved in a suitable solvent, if desired, with adjuvant. Antiseptics are also available, if necessary. Illustrative of solvents, are distilled water, physiological saline and phosphate-buffered aqueous sodium chloride solution. As adjuvants, aluminum hydroxide, aluminum phosphate, calcium phosphate, alum and Freund's incomplete adjuvant are exemplified. The amount of the adjuvant may be appropriately selected from the range of amounts being necessary and sufficient for increasing the immunoactivity. Thimerosal, phenol, benzoic acid and formalin are exemplified as antiseptics.

When immunization is carried out 2 to 3 times per week (without adjuvant), 1 to 50 γ/kg of protease toxoid is administered to human beings, preferably with 0.1 to 10 γ/kg of OEP and 1 to 50 γ/kg of elastase toxoid. Depending on the state of immunization, the amounts may be increased appropriately. In the case of minks, 10 to 2000γ/head of elastases toxoid is administered preferably with 10 to 2000 γ/head of OEP, 10 to 2000 γ/head of protease toxoid and adjuvant, when immunization is carried out two times for preventive vaccinations. For therapeutic vaccinations for mink, 10 to 2000 γ/head of protease toxoid is administered with 10 to 2000 γ/head of elastase toxoid and 0.1 to 100 γ/head of OEP with or without adjuvant.

Practical and presently preferred embodiments of the invention are illustratively shown in the following examples.

EXAMPLE 1

Crystalline protease of *P. aeruginosa* (100 mg) is dissolved in 0.05 M solution of sodium hydrogenphosphate (pH 8.5) (100–200 ml) containing 0.005–0.2 M lysine. To the solution is added formalin until the concentration reaches about 1–8% (v/v). After being allowed to stand at room temperature for 3 days, the mixture is dialyzed against water and lyophylized to yield the toxoid of protease. The yield is 98–100%.

The remaining protease activity is examined by the method described in Method (a) of Experiment 2 after the dialysis for 3 days. The results are shown in Tables 5 and 6.

Table 5

| Concentration of Formalin | Remaining Protease Activity (%) |
|---|---|
| 8 | 21 |
| 4 | 42 |
| 1 | 93 |
| 0 | 100 |

Note:
The concentrations of toxoid and lysine are 1 mg/ml and 0.05 M, respectively.

Table 6

| Concentration of Lysine | Remaining Protease Activity (%) |
|---|---|
| 0 | 88 |
| 0.05 | 21 |
| 0.1 | 9 |
| 0.2 | <5 |
| Control* | 100 |

Note:
The concentrations of toxoid and formalin are 1mg/ml and 8%, respectively.
*no addition of formalin

EXAMPLE 2

The toxoid is prepared in the same manner as in Example 1 using 0.5 M oxymethanesulfinic acid in place of formalin in the presence of 0.05 M lysine. The remaining protease activity is 15%.

EXAMPLE 3

The toxoid is prepared in the same manner as in Example 1 using 2.5 M oxymethanesulfinic acid in place of formalin in the presence of 0.05 M lysine. Protease activity completely disappeared.

EXAMPLE 4

A solution of highly purified elastase containing 10–15 mg enzyme protein/ml (50 mPU*/1 mg of enzyme protein), 5 M sodium chloride, 10 mM sodium acetate, 2 mM calcium chloride, 10 mM sodium acetate, 2 mM calcium chloride and 0.1 mM zinc chloride is diluted with borate buffer (pH 9.0 ) or 0.2 M sodium acetate solution (pH 9.0) until the concentration of the enzyme protein reaches 2–5 mg/ml (the final concentration of borate is about 0.2 M). To the solution is added formalin until the final concentration becomes 0.5–4% (v/v). The mixture is allowed to stand at room temperature for 3–6 days. Elastase activity almost completely disappears in one day. The inactivated solution of elastase is dialyzed against water and then is lyophilized to yield the toxoid of elastase. The yield is about 60–100%.

Note: * mPU = milli protease unit, 1 PU means that 1 mg of tyrosine is produced by proteinase for 1 hour. One mPU is 1/1000 of 1 PU.

The remaining elastase activity is examined by the method noted in Example 1 and the results are shown in Table 7.

Table 7

| Concentration of Formalin | Remaining Elastase Activity (%) | |
|---|---|---|
| | Borate Buffer | Sodium Acetate |
| 4 | ≦5 | 21 |
| 2 | ≦5 | 45 |
| 1 | ≦5 | — |
| 0.5 | 9 | — |

Note:
The concentration of the enzyme protein is 2 mg/ml. The mixture is kept at room temperature for 3 days after the addition of formalin.

EXAMPLE 5

The toxoid of elastase is prepared in the same manner as in Example 4 using 0.2 M sodium acetate solution (pH 9.0), but oxymethanesulfinic acid is employed in place of formalin. The elastase solution is kept at room temperature for 3 and 6 days after the addition of oxymethanesulfinic acid. The remaining elastase activity is examined in the same manner as in Example 4 and the results are shown in Table 8.

Table 8

| Concentration of oxymethanesulfinic acid | Remaining Elastase Activity | |
|---|---|---|
| | 3 days | 6 days |
| 3 | 10 | ≦5 |
| 2 | 8 | ≦5 |
| 1 | 17 | ≦5 |
| 0.5 | 38 | ≦5 |
| 0.25 | 47 | ≦5 |
| 0 | 100 | 100 |

What is claimed is:

1. Toxoid derived from protease of *Pseudomonas aeruginosa*, which is obtained by inactivating the purified protease by treating purified protease produced from *Pseudomonas aeruginosa* in a suitable buffer solution with 4–10% formalin or 0.04–3M oxymethanesulfinic acid in the presence of lysine, with the subsequent steps of dialysis and lyophilization, said toxoid having the following physicochemical properties:
   (1) molecular weight: 63,000 (gel filtration)
   (2) ultraviolet absorption spectrum: maximum 280 mμ ($E_{1\%}^{280}$ 9.27 0.1 M KCl), minimum 250 mμ
   (3) isoelectric point: pH 5.2 (forcal electrophoresis)
   (4) constituent amino acids: (amino acid (g)/100 g of protein) aspartic acid (15.6), glutamic acid (9.5), leucine (8.7), alanine (8.5), glycine (7.7), serine (7.6), tyrosine (6.9), phenylalanine (5.9), theronine (5.0), valine (5.0), lysine (4.1), isoleucine (3.9), arginine (2.3), tryptophan (2.3), proline (2.1), histidine (1.9), ammonia (1.4) (total 98.5 g)
   (5) appearance: colorless powder
   (6) antigen activity: positive
   (7) protease activity: negative.

2. Toxoid derived from the elastase of *Pseudomonas aeruginosa*, which is obtained by inactivating the purified elastase produced from *Pseudomonas aeruginosa* in a suitable buffer solution with 1–6% formalin or 0.25–5M oxymethanesulfinic acid with the subsequent steps of dialysis and lyophilization, said toxoid having the following physicochemical properties:
(1) molecular weight: 47000 (gel filtration)
(2) ultraviolet absorption spectrum: maximum 278 m$\mu$ ($E_{1\%}^{278}$ 21.2, 0.1 M KCl), minimum 252 m$\mu$
(3) isoelectric point: pH 6.5 (electrophoresis with cellulose acetate membrane)
(4) constituent amino acids: (amino acid (g)/100 g of protein) aspartic acid (14.2), tyrosine (9.9), phenylalinine (7.0), glutamic acid (6.5), arginine (6.5), alanine (5.8), glycine (5.6), serine (5.6), threonine (5.0), valine (4.9), leucine (4.3), lysine (3.9), methionine (2.9), proline (2.9), isoleucine (2.7), histidine (2.6), tryptophan (2.3), cystine/2 (1.2), ammonia (0.9) (total 94.7 g)
(5) appearance: colorless powder
(6) antigen activity: positive
(7) elastase activity: negative.

3. A method for preventing infections caused by *Pseudomonas aeruginosa* by inoculating the toxoid claimed in claim 1 in a sufficient quantity to produce protease antibody.

4. A method for preventing infections caused by *Pseudomonas aeruginosa* by inoculating the toxoid claimed in claim 2 in a sufficient quantity to produce elastase antibody.

5. An anti-serum for preventing and treating infections caused by *Pseudomonas aeruginosa* which is obtained from human or animal serum by inoculating the toxoid claimed in claim 1.

6. An anti-serum for preventing and treating infections caused by *Pseudomonas aeruginosa* which is obtained from human or animal serum by inoculating the toxoid claimed in claim 2.

7. The toxoid according to claim 1, wherein the protease is treated with formalin.

8. The toxoid according to claim 1, wherein the formalin is in a concentration of 8%.

9. The toxoid according to claim 2, wherein the elastase is treated with formalin.

10. The toxoid according to claim 7, wherein the buffer solution is at pH 6 to 10.

11. The toxoid according to claim 8, wherein the buffer solution is at pH 6 to 10.

12. The toxoid according to claim 9, wherein the buffer solution is at pH 6 to 10.

13. The toxoid according to claim 7, wherein the buffer solution is at pH 9.

14. The toxoid according to claim 8, wherein the buffer solution is at pH 9.

15. The toxoid according to claim 9, wherein the buffer solution is at pH 9.

16. The toxoid according to claim 1, wherein the buffer solution is phosphate buffer.

17. The toxoid according to claim 2, wherein the buffer solution is borate buffer.

18. The toxoid according to claim 1, wherein the lysine is in a concentration of 0.05 to 0.2 M.

19. The method according to claim 3, wherein 1 to 50 $\gamma$/kg of protease toxoid is administered to immunize human beings.

20. The method according to claim 19, wherein the immunization is carried out 2 to 3 times per week.

21. The method according to claim 4, wherein 10 to 2000 $\gamma$/head of elastase toxoid is administered to immunize mink.

22. The method according to claim 21, wherein the immunization is carried out two times for preventive vaccinations.

* * * * *